United States Patent [19]

Sprecker et al.

[11] 4,147,727

[45] * Apr. 3, 1979

[54] 1-BUTENOYL-3,3-DIMETHYLCYCLOHEX-ANE MIXTURES

[75] Inventors: Mark A. Sprecker, Sea Bright; Manfred H. Vock, Locust; Frederick L. Schmitt, Holmdel; John B. Hall, Rumson; James M. Sanders, Eatontown, all of N.J.

[73] Assignee: International Flavors & Fragrances Inc., New York, N.Y.

[*] Notice: The portion of the term of this patent subsequent to Apr. 3, 1996, has been disclaimed.

[21] Appl. No.: 851,726

[22] Filed: Nov. 15, 1977

Related U.S. Application Data

[60] Division of Ser. No. 740,948, Nov. 11, 1976, Pat. No. 4,081,481, which is a continuation-in-part of Ser. No. 713,357, Aug. 11, 1976, Pat. No. 4,062,894.

[51] Int. Cl.² .............................................. C07C 49/61
[52] U.S. Cl. ................................ 260/586 R; 252/522; 426/538
[58] Field of Search ..................................... 260/586 R

[56] References Cited

U.S. PATENT DOCUMENTS

| | | | |
|---|---|---|---|
| 3,592,856 | 7/1971 | Offenhauser et al. | 260/586 R |
| 3,822,315 | 7/1974 | Klein | 260/586 R |
| 3,887,625 | 6/1975 | Schulte-Elte | 260/586 R |
| 3,920,751 | 11/1975 | Chabardis et al. | 260/586 R |
| 3,923,896 | 12/1975 | Schulte-Elte | 260/586 R |
| 3,956,392 | 5/1976 | de Haan et al. | 260/586 R |

FOREIGN PATENT DOCUMENTS 7500838 7/1975 Netherlands ........................ 260/586 R

*Primary Examiner*—Norman Morgenstern
*Attorney, Agent, or Firm*—Arthur L. Liberman; Franklin D. Wolffe; Harold Haidt

[57] ABSTRACT

1-butenoyl-3,3-dimethylcyclohexane mixtures having a sweet rootbeer-like, cedarwood flavor useful as flavorants in foodstuffs are described.

1 Claim, No Drawings

1-BUTENOYL-3,3-DIMETHYLCYCLOHEXANE MIXTURES

This application is a divisional of application for United States Letter Patent, Ser. No. 740,948, filed on Nov. 11, 1976, now U.S. Pat. No. 4,081,481, which, in turn, is a continuation-in-part of U.S. application for Letters Patent, Ser. No. 713,357, filed on Aug. 11, 1976, now U.S. Pat. No. 4,062,894, issued on Dec. 13, 1977.

BACKGROUND OF THE INVENTION

The present invention relates to 1-butanoyl-3,3-dimethylcyclohexane having the structure:

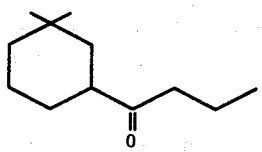

and novel compositions using such 1-butanoyl-3,3-dimethylcyclohexanes to augment or enhance the aroma of perfume compositions, colognes and perfumed articles.

There has been considerable work performed relating to substances which can be used to impart (modify, augment or enhance) fragrances to (or in) various perfume compositions, perfumed articles and colognes. These substances are used to diminish the use of natural materials, some of which may be in short supply and to provide more uniform properties in the finished product.

Fruity, berry, herbaceous aromas with green and tobacco nuances are desirable in several types of perfume compositions, perfumed articles and colognes.

Acetylcyclohexane and 1-acetyl-3,3-dimethylcyclohexane are known substituents in perfumery. Thus, Arctander, "Perfume and Flavor Chemicals (Aroma Chemicals)," published in 1969, discloses acetylcyclohexane in Volume I, number 36:

"Peculiar camphoraceous-sweet odor with a certain amount of floral tones.

Although this chemical would primarily lend itself to perfume compositions in the Pine, Wood, Herbaceous and other non-floral types, it has a similarity to the harsh-floral types such as Hyacinth, etc. and its sweetness is sometimes classified as 'musky.'"

1-Acetyl-3,3-dimethylcyclohexane is disclosed as a fragrance material in U.S. Pat. No. 3,487,102 issued on Dec. 30, 1969.

The fragrance properties of the aforementioned acetyldimethylcyclohexane derivatives are different in kind from the fragrance properties of the compound of the instant invention.

Firmenich's Dutch published application 7500838 discloses the preparation of the compound having the structure:

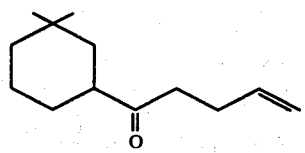

and discloses its use in perfumery and in augmenting foodstuff flavors. The perfumery use of this compound and other members of its class as "floral, green, herbaceous and chypre" useful in galbanum resinoids is also disclosed.

The compounds disclosed in Dutch published application 7500838 have organoleptic properties which cause them to be different in kind from the 1-butanoyl-3,3-dimethylcyclohexane of our invention, which has unobvious, unexpected and advantageous characteristics in the field of augmenting or enhancing the organoleptic impressions of perfumes, colognes and perfumed articles.

THE INVENTION

It has now been discovered that novel perfume compositions, colognes and perfumed articles having fruity, berry, hergaceous aromas with green and tobacco nuances may be provided by the utilization of 1-butanoyl-3,3-dimethylcyclohexane having the formula:

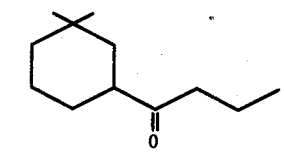

The 1-butanoyl-3,3-dimethylcyclohexane useful as indicated supra may be produced preferably by a process which comprises the reaction of 1-acetyl-3,3-dimethylcyclohexane with acetaldehyde in the presence of an inorganic base or a mixture of boron oxide ($B_2O_3$) and boric acid, thereby producing a compound having the structure:

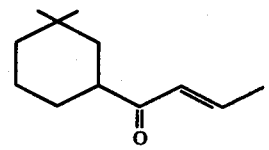

(mixture of "cis" and "trans" isomers) and a compound having the structure:

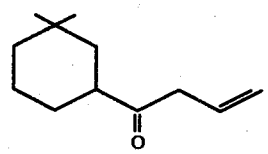

and then reducing the resulting product with hydrogen thereby producing a compound having the structure:

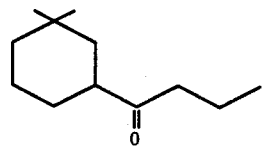

The first reaction with acetaldehyde is carried out at a temperature of from about 20° C. up to 160° C., when using a catalyst which is an inorganic base, such as an alkali metal hydroxide, for example, potassium hydroxide, sodium hydroxide and lithium hydroxide or an alkaline earth metal hydroxide such as barium hydroxide or lithium hydroxide; or at a temperature in the range of from about 100° C. up to 200° C. when using a catalyst which is a mixture of boric acid (HBO₃) and boron oxide.

The time of reaction is inversely proportional to the temperature of reaction. Thus, when using a mixture of boric acid and boron oxide the time of reaction varies between 2 and 10 hours and when using a higher temperature, the time of reaction varies from between 1 and 8 hours.

When using an inorganic base, the mole ratio of inorganic base:1-acetyl-3,3-dimethylcyclohexane may vary from 0.1:1 up to 2:1 with a mole ratio of 1:1 being preferred. When using the mixture of boric acid and boron oxide, the mole ratio of boron oxide:1-acetyl-3,3-dimethylcyclohexane varies from 0.5:1 up to 1.5:1 with a mole ratio of 1:1 being preferred. The concentration of boric acid in the reaction mass may vary from 1 up to 80 grams per mole of acetaldehyde.

In all cases the mole ratio of acetaldehyde:1-acetyl-3,3-dimethylcyclohexane may vary from 1:1 up to about 3:1 with a mole ratio of 2:1 being preferred.

The reactions may take place in the presence or in the absence of an inert solvent. When using boric acid or boric oxide, the reaction preferably is carried out without solvent. When using an inorganic base catalyst, the reaction preferably takes place using a solvent such as methanol, ethanol or isopropanol.

The reduction reaction to form the compound having the structure:

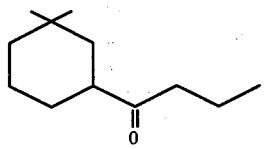

is carried out preferably in the presence of inert solvents such as isopropyl alcohol; at hydrogenation pressures of between 50 and 15- psig; at temperatures of between 25° and 150° C., and using hydrogenation catalysts such as 5% palladium-on-carbon, rhodium, platinum and Raney nickel. The time of reaction varies inversely with the temperature and pressure of reaction. Thus, lower pressures and temperatures give rise to a need for greater times of reaction. Thus, the time of reaction may vary from 1 hour up to 5 hours.

The previous reaction sequence is illustrated as follows:

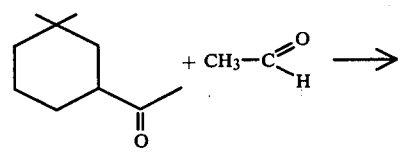

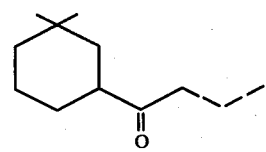

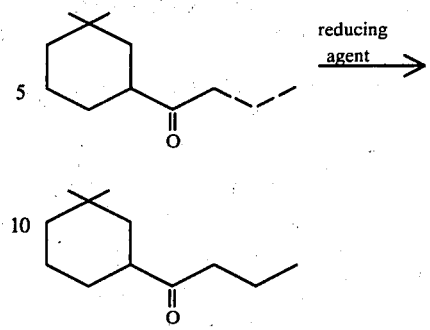

wherein one of the dashed lines represents a carbon-carbon double bond and the other of the dashed lines represents a carbon-carbon single bond.

The 1-butanoyl-3,3-dimethylcyclohexane of our invention and one or more auxiliary perfume ingredients, including, for example, alcohols, aldehydes, nitriles, esters, cyclic esters (or lactones) and natural essential oils, may be admixed so that the combined odors of the individual components produce a pleasant and desired fragrance, particularly and preferably in amber fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low-boiling, fresh-smelling materials.

In perfume compositions, it is the individual components which contribute to their particular olfactory characteristics; however, the overall sensory effect of the perfume composition will be at least the sum total of the effects of each of the ingreduents. Thus, the 1-butanoyl-3,3-dimethylcyclohexene can be used to alter, modify or enhance the aroma characteristics of a perfume composition, for example, by utilizing or moderating the olfactory reaction contributed by another ingredient in the composition.

The amount of 1-butanoyl-3,3-dimethylcyclohexane of our invention which will be effective in perfume compositions as well as in perfumed articles and colognes depends on many factors, including the other ingredients, their amounts and the effects which are desired. It has been found that perfume compositions containing as little as 0.01% of a 1-butanoyl-3,3-dimethylcyclohexane or even less (e.g., 0.005%) can be used to impart a fruity, berry, herbaceous aroma with green and tobacco nuances to soaps, cosmetics or other products. The amount employed can range up to 70% of the fragrance components and will depend on considerations of cost, nature of the end product, the effect desired on the finished product and the particular fragrance sought.

The 1-butanoyl-3,3-dimethylcyclohexane of our invention is useful [taken alone or together with other ingredients in perfume compositions] as an olfactory component(s) in detergents and soaps, space odorants and deodorants, perfumes, colognes, toilet water, bath preparations, such as lacquers, brilliantines, pomades and shampoos; cosmetic preparations, such as creams, deodorants, hand lotions and sun screens; powders, such as talcs, dusting powders, fact powders and the like. When used as an olfactory component as little as 1% of the 1-butanoyl-3,3-dimethylcyclohexane will suffice to impart an intense herbaceous note to amber formulations. Generally no more than 3% of the 1-butanoyl-3,3-dimethylcyclohexane based on the ultimate end product is required in the perfume composition.

In addition, the perfume composition or fragrance composition of our invention can contain a vehicle or carrier for the 1-butanoyl-3,3-dimethylcyclohexane. The vehicle can be a liquid such as a non-toxic alcohol, a non-toxic glycol, or the like. The carrier can also be an absorbent solid such as a gum (e.g., gum arabic) or components for encapsulating the composition (such as gelatin).

It will thus be apparent that the 1-butanoyl-3,3-dimethylcyclohexane of our invention can be utilized to alter, modify or enhance fragrances of a wide variety of consumable materials.

The following examples serve to illustrate our invention, and this invention is to be considered restricted thereto only as indicated in the appended claims.

All parts and percentages given herein are by weight unless otherwise specified.

EXAMPLE I

SYNTHESIS OF 1-(3,3-DIMETHYLCYCLOHEXYL)-CIS and TRANS-(2 and 3)-BUTEN-1-ONE

Reaction:

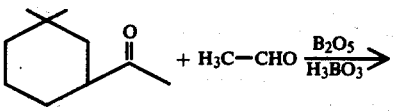

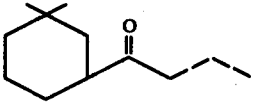

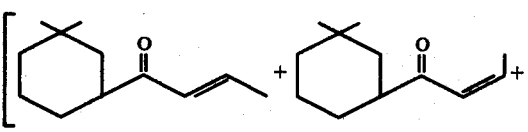

A mixture of 616 grams of 1-acetyl-3,3-dimethylcyclohexane (4 moles), 132 grams of acetaldehyde (3 moles), 105 grams boron oxide (1.5 moles) and 12 grams of boric acid (0.2 moles) is heated at 150° C. in an autoclave for 3 hours. After cooling to room temperature the solution is filtered from inorganic salts, washed once with aqueous sodium carbonate and twice with saturated salt solution. Distillation through a short column afforded 127.2 grams of 1-acetyl-3,3-dimethylcyclohexane and 127.2 grams of a mixture of 1-(3,3-dimethylcyclohexyl)-cis and trans-2-buten-1-one and 1-(3,3-dimethylcyclohexyl)-3-buten-1-one.

A portion of the distillate rich in the desired product(s) was distilled through a 1"×12" Goodloe column giving the following fractions:

| Fraction No. | Vapor Temp. (° C.) | Liquid Temp. (° C.) | Vacuum (mm Hg) | Weight (g) | Reflux Ratio |
|---|---|---|---|---|---|
| 1 | 67-70 | 89-91 | 4.4-4.7 | 37.9 | 2:1 |
| 2 | 70 | 95 | 4.9 | 40.9 | 2:1 |
| 3 | 70 | 103 | 5.0 | 40.1 | 2:1 |
| 4 | 74 | 113 | 5.0 | 29.9 | 2:1 |
| 5 | 100 | 116 | 5.4 | 16.7 | 9:1 |
| 6 | 102 | 123 | 4.8 | 17.1 | 9:1 |
| 7 | 102 | 125 | 5.0 | 29.2 | 9:1 |
| 8 | 112 | 131 | 8.2 | 20.7 | 9:1 |
| 9 | 106 | 139 | 5.7 | 22.8 | 9:1 |
| 10 | 104 | 154 | 5.2 | 13.3 | 9:1 |
| 11 | 104 | 179 | 5.3 | 11.3 | 9:1 |
| 12 | 100 | 202 | 5.2 | 6.7 | 9:1 |

Bulked fractions 6–10 at 2 ppm, have a cedarwood aroma and a sweet, rootbeer-like, cedarwood flavor.

The mass spectral analysis is as follows:
180/69, 41, 39, 55, 165, 27.

The NMR analysis is as follows:

| 0.94 ppm. (s) | gem dimethyl protons | 6 H |
| 1.74-1.08 (m) | —CH$_2$— | 8 H |
| 1.90 (doublet with allylic coupling) | CH$_3$—C=C—C(=O)— | 3 H |
| 2.74 (m) | HC—C(=O)— | 1 H |
| 6.18 (broad doublet) | —C(=O)—C(H)=C— | 1 H |
| 7.04-6.70 (m) | —C(=O)—C=C(H)— | 1 H |

The IR analysis is as follows:
960 cm$^{-1}$, 1290, 1360, 1380, 1440, 1625, 1670, 1690, 2860, 2940.

EXAMPLE II

HYDROGENATION OF 1-(3,3-DIMETHYLCYCLOHEXYL)-CIS AND TRANS-(2 and 3)-BUTEN-1-ONE Reaction:

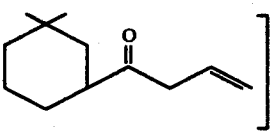

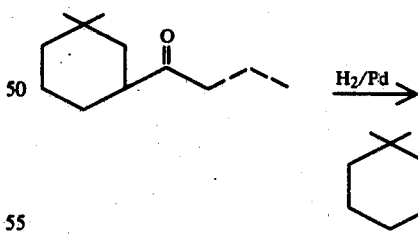

Into a 250 cc Parr shaker is placed 107 grams (6 moles) of 1-(3,3-dimethylcyclohexyl)-cis and trans-(2 and 3)-buten-1-one prepared according to Example I, 1 gram of 5% Palladium-on-carbon catalyst and 125 grams of isopropyl alcohol. The Parr shaker is sealed and heated to a temperature of 125° C. at a pressure of 50–150 psig of hydrogen and maintained at that pressure range and temperature range for a period of 1.5 hours. At the end of the 1.5 hour period the reaction product is filtered, the solvent is removed in vacuo, and the residual oil is distilled on a 8 plate Vigreaux column. The distillation data follows:

| Fraction No. | Vapor Temp. (° C.) | Liquid Temp. (° C.) | Vacuum (mm Hg) | Weight (g) | Reflux Ratio |
|---|---|---|---|---|---|
| 1 | 86-89 | 100 | 4.6 | 9.0 | 11:1 |
| 2 | 90 | 102 | 4.7 | 12.0 | 11:1 |
| 3 | 90 | 102 | 4.6 | 8.8 | 11:1 |
| 4 | 90 | 102 | 4.7 | 11.5 | 11:1 |
| 5 | 90 | 105 | 4.6 | 14.0 | 11:1 |
| 6 | 90 | 110 | 4.6 | 13.5 | 11:1 |
| 7 | 90 | 113 | 4.6 | 8.4 | 11:1 |
| 8 | 90 | 141 | 4.6 | 11.1 | 11:1 |
| 9 | 90 | 205 | 4.6 | 4.4 | 11:1 |

From a perfumery standpoint fraction 7 at 10% in food grade alcohol has a fruity, berry, herbaceous aroma with green, tobacco nuances.

The mass spectral analysis is as follows:
182/111, 69, 43, 41, 71, 55, 27.

The NMR analysis is as follows (fraction 8):

| 0.90 ppm | (t) | $CH_3-CH_2-$ | 3 H |
|---|---|---|---|
| 0.91 ppm | (s) | dimethyl protons | 6 H |
| 1.95 – 1.16 | (m) | $-CH_2-$ | 10 H |
| 2.49 | (t) | $-CH_2-CH_2-\overset{O}{\underset{\|}{C}}-$ | 2 H |
| 2.69 – 2.31 | (m) | $HC-\overset{O}{\underset{\|}{C}}-$ | 1H |

The IR analysis (fraction 8) is as follows:
1020 cm$^{-1}$, 1120, 1175, 1290, 1360, 1375, 1400, 1455, 1705, 2860, 2930.

EXAMPLE III

A perfume composition is prepared by admixing the following ingredients in the indicated proportions:

| Ingredient | Amount (Grams) |
|---|---|
| n-Decyl Aldehyde | 1 |
| n-Dodecyl Aldehyde | 2 |
| Methyl Nonyl Acetaldehyde | 0.5 |
| Linalool | 50 |
| Linalyl Acetate | 70 |
| Phenyl Ethyl Alcohol | 100 |
| Petigrain SA | 20 |
| Bergamot Oil | 30 |
| Alpha Methyl Ionone | 25 |
| 1-(3,3-dimethylcyclohexyl)-butan-1-one produced according to Example II | 10 |
| Cyclized Bicyclo C-12 material produced according to the process of Example IV of Canadian Patent 854,225 issued on October 20, 1970 | 5 |
| Isobornyl Cyclohexyl Alcohol | 10 |
| Benzyl Acetate | 25 |
| 2-n-Heptylcyclopentanone | 5 |
|  | 353.3 (TOTAL) |

The foregoing blend is evaluated and found to have a high degree of richness and persistence in its novel natural amber quality. This base composition can be admixed with aqueous ethanol, chilled and filtered to produce a finished cologne. The cologne so prepared has an amber aroma leaning towards a woody amber note with excellent fruity and herbacenous nuances. The base composition can also be used to scent soap or other toilet goods such as lotion, aerosol, sprays and the like.

EXAMPLE IV

PREPARATION OF A COSMETIC-POWDER COMPOSITION

A cosmetic powder is prepared by mixing in a ball mill, 100 g of talcum powder with 0.25 g of 1-(3,3-dimethylcyclohexyl)-butan-1-one prepared according to Example II. It has an excellent fruity, berry, herbaceous aroma with green and tobacco nuances.

EXAMPLE V

PERFUMED LIQUID DETERGENT

Concentrated liquid detergents (lysine salt of n-dodecyl-benzene sulfonic acid as more specifically described in U.S. Pat. No. 3,948,818 issued on Apr. 6, 1976) with a herbaceous odor are prepared containing 0.10%, 0.15% and 0.20% of 1-(3,3-dimethylcyclohexyl)-butan-1-one prepared according to Example II. They are prepared by adding and homogeneously mixing the appropriate quantity of 1-(3,3-dimethylcyclohexyl)-butan-1-one in the liquid detergent. The detergents all possess a herbaceous fragrance with green and tobacco nuances, the intensity increasing with greater concentrations of 1-(3,3-dimethylcyclohexyl)-butan-1-one.

EXAMPLE VI

PREPARATION OF A COLOGNE AND HANDKERCHIEF PERFUME 1-(3,3-Dimethylcyclohexyl)-butan-1-one prepared according to the process of Example II is incorporated in a cologne at a concentration of 2.5% in 85% aqueous ethanol; and into a handkerchief perfume at a concentration of 20% (in 95% aqueous ethanol). A distinct and definite herbaceous fragrance is imparted to the cologne and to the handkerchief perfume.

EXAMPLE VII

PREPARATION OF A COLOGNE AND HANDKERCHIEF PERFUME

The composition of Example III is incorporated in a cologne at a concentration of 2.5% in 85% aqueous ethanol; and into a handkerchief perfume at a concentration of 20% (in 95% aqueous ethanol). The use of 1-(3,3-dimethylcyclohexyl)-butan-1-one in the composition of Example III affords a distinct and definite strong amber aroma with herbaceous and tobacco notes to the handkerchief perfume and cologne.

EXAMPLE VIII

PREPARATION OF SOAP COMPOSITION

One hundred grams of soap chips are mixed with one gram of 1-(3,3-dimethylcyclohexyl)-butan-1-one of Example II until a substantially homogeneous composition is obtained. The perfumed soap composition manifests an excellent fruity, berry, tobacco aroma with green and tobacco nuances.

EXAMPLE IX

PREPARATION OF A DETERGENT COMPOSITION

A total of 100 g of a detergent powder (Lysine salt of n-dodecyl benzene sulfonic acid as more specifically described in U.S. Pat. No. 3,948,818 issued Apr. 6, 1976) is mixed with 0.15 g of the 1-(3,3-dimethylcyclohexyl)-butan-1-one of Example II until a substantially homoge-

What is claimed is:
1. A mixture of 1-butenoyl-3,3-dimethylcyclohexanes represented by the structure:
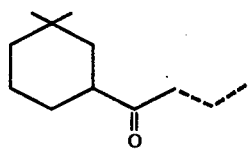
wherein said mixture consists of compounds having the structure:
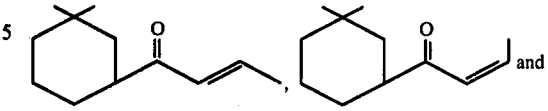
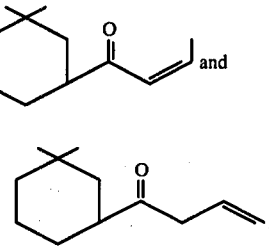
and wherein one of the dashed lines represents a carbon-carbon single bond and the other of the dashed lines represents a carbon-carbon double bond.
* * * * *